United States Patent
Schweighardt et al.

(10) Patent No.: US 7,343,781 B2
(45) Date of Patent: Mar. 18, 2008

(54) SYSTEMS AND METHODS FOR DETECTING LIQUID PARTICLES IN A GAS SYSTEM

(75) Inventors: Frank Kenneth Schweighardt, Allentown, PA (US); David Hon Sing Ying, Allentown, PA (US); Dean Anthony Chin-Fatt, Schnecksville, PA (US); Kevin Boyle Fogash, Wescosville, PA (US); Charles Randall Kayhart, Alburtis, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 211 days.

(21) Appl. No.: 11/249,206

(22) Filed: Oct. 13, 2005

(65) Prior Publication Data

US 2007/0086007 A1  Apr. 19, 2007

(51) Int. Cl.
*G01N 21/00* (2006.01)
(52) U.S. Cl. .................... 73/28.01; 356/337
(58) Field of Classification Search ........... 73/28.01; 356/337
See application file for complete search history.

(56) References Cited

U.S. PATENT DOCUMENTS

| | | | | |
|---|---|---|---|---|
| 5,027,642 A | * | 7/1991 | Wen et al. | 73/23.2 |
| 5,369,981 A | * | 12/1994 | Merz et al. | 73/28.01 |
| 5,642,193 A | | 6/1997 | Girvin et al. | |
| 5,864,399 A | | 1/1999 | Girvin et al. | |
| 5,932,795 A | * | 8/1999 | Koutrakis et al. | 73/28.01 |
| 6,709,478 B2 | * | 3/2004 | Schlaps | 55/417 |

FOREIGN PATENT DOCUMENTS

DE  101 62 278 A1  7/2003

OTHER PUBLICATIONS

Ensuring the Purity of CO2 and Other Process Gases; Thermo Andersen brochures Apr. 2002.

* cited by examiner

*Primary Examiner*—Daniel S. Larkin
(74) *Attorney, Agent, or Firm*—Michael K. Boyer

(57) ABSTRACT

A system for detecting fine liquid, e.g., oil, particles in a gas system having a high pressure compressor and at least two gas handling devices, e.g., a coalescer and at least one adsorber. The detection system uses plural sensors and a monitor unit to detect the presence of such fine liquid particles in various portions of the gas system and to provide alert signals in response thereto. The alert signals can be used by associated valves to control the gas system.

24 Claims, 1 Drawing Sheet

SYSTEMS AND METHODS FOR DETECTING LIQUID PARTICLES IN A GAS SYSTEM

BACKGROUND OF THE INVENTION

This invention relates generally to liquid particle/droplet detecting systems, and more particularly to systems for detecting particles or droplets of liquids, e.g., oils, solvents, aqueous liquids, etc., in gas systems making use of at least one high pressure gas compressor or other device which may introduce fine particles of such liquid(s) into gas in the system.

As should be appreciated by those skilled in the art, in gas producing, transport and/or storage systems that make use of high pressure gas compressors, it is highly likely that there will be some oil leakage from the seals of such compressors, which leakage is typically in the form of minute particles or droplets introduced into the gas stream (sometimes referred to as "oil droplet breakthrough"). Since the existence of such particles will contaminate the gas product, it is a common practice to make use of separators, coalescers, adsorbent beds, and filters in gas systems downstream of the high pressure gas compressor (or any other device which may introduce fine oil particles into the gas). Such devices are designed to capture such oil particles and thereby prevent them from contaminating the final gas product.

The patented prior art includes various particle detecting devices that make use of light scattering techniques to detect the presence of particles in fluid streams. For example, in U.S. Pat. No. 5,864,399 (Girvin et al.) and U.S. Pat. No. 5,642,193 (Girvin et al.) there are disclosed particle detectors, each of which employs a laser disposed in a resonant cavity and an intra-cavity view volume. The resonant cavity is defined by two spaced apart mirrors, with the laser medium positioned between them, defining a light path. A pump source is optically coupled to drive the laser medium to produce coherent light having a first wavelength. The view volume is positioned in the light path, between the first mirror and the laser medium, to introduce particles into the resonant cavity so that light impinging there-upon produces scattered light. A detector is disposed to sense light scattered from the view volume and produces signals proportional to the light sensed. A displaying device, such as a pulse height analyzer, is in electrical communication to receive the signals produced by the detector to quantitatively display the intensity of the light sensed.

DE 10162278 discloses a system of detecting the presence of air compressor produced oil droplets in compressed gas stream by heating and expanding a partial aerosol stream, to thereby transform the droplets into a gas which is subsequently analyzed by a gas sensor.

Devices for detecting particles in a fluid stream are also commercially available. For example, Thermo Andersen, Inc., of Franklin, Mass. sells a HPM-1000 particulate monitor that is designed to be installed directly in line with compressed air/gas streams to provide continuous measurement of oil mist carryover, entrained water mist, and particulate contamination at pressures up to 350 psig. The HPM-1000 monitor uses a high sensitivity nephalometric (photometric) sensor, whose light scattering detection configuration has been optimized for the measurement of fine particle contamination in compressed air and gas streams.

While the aforementioned prior art is generally suitable for its intended purposes, it never the less leaves something to be desired from the standpoint of providing an on-line process monitoring system and method capable of detecting low levels of fine oil particles in a post compressor gas stream (or in a gas stream from any other device which may introduce fine oil particles into the stream) and, to alert an operator to a failure of the compressor seal before the oil is passed into the final product or to institute automatic remedial action, e.g., shut off at least a part of the system and/or bring another part of the system on-line to prevent the further contamination of the gas product.

The disclosure of the previously identified patents, patent applications and publications is hereby incorporated by reference.

The subject invention addresses those needs by providing systems and methods to aid in prevention of breakthrough of fine oil (or other liquid) particles into a downstream gas supply by monitoring the gas after the compressor at several points and reacting to any appreciable increase in oil levels. Moreover, the monitoring system is capable of detecting extremely low levels of oil particles. Thus, the usage of the systems and methods of this invention enables a more optimal usage of existing adsorbent beds and coalescers and does not require the transformation of the oil droplets into a gas.

BRIEF SUMMARY OF THE INVENTION

A detection system and method for detecting the presence of fine liquid, e.g., oil, particles in a gas system. The gas system comprises a compressor and at least a first gas handling device, a second gas handling device, a first gas-carrying conduit connected between the compressor and the first device and a second gas-carrying conduit connected between the first device and the second device. The first and second devices are connected in series downstream of the compressor by the gas-carrying conduits. The first device has a first valve, e.g., a blow-down valve, associated with it. The second device has a second valve, e.g., a diverter valve, associated with it. The compressor is susceptible to introduce fine oil particles into the first gas-carrying conduit.

The detection system comprises a data acquisition unit, e.g., a data logger, computer or portion of a distributed control system, at least a first monitor and a second monitor. Each of the monitors is arranged for detecting the presence of the fine liquid, oil, particles in a gas by means of light scattering and for providing an output signal to the data acquisition unit monitor unit in response to the detection of such fine liquid particles. The first monitor is in communication with the interior of the first gas-carrying conduit. The second monitor is in communication with the interior of the second gas-carrying conduit. The data acquisition unit is arranged to provide at least one output signal concerning the detection of the fine liquid particles in the gas system.

In accordance with one aspect of this invention the at least one output signal of the data acquisition unit comprises a humanly perceptible signal. In accordance with another aspect of this invention the at least one output signal of the data acquisition unit is coupled to the first and second valves for effecting the selective operation of those valves.

DETAILED DESCRIPTION OF THE INVENTION

Figure 1:
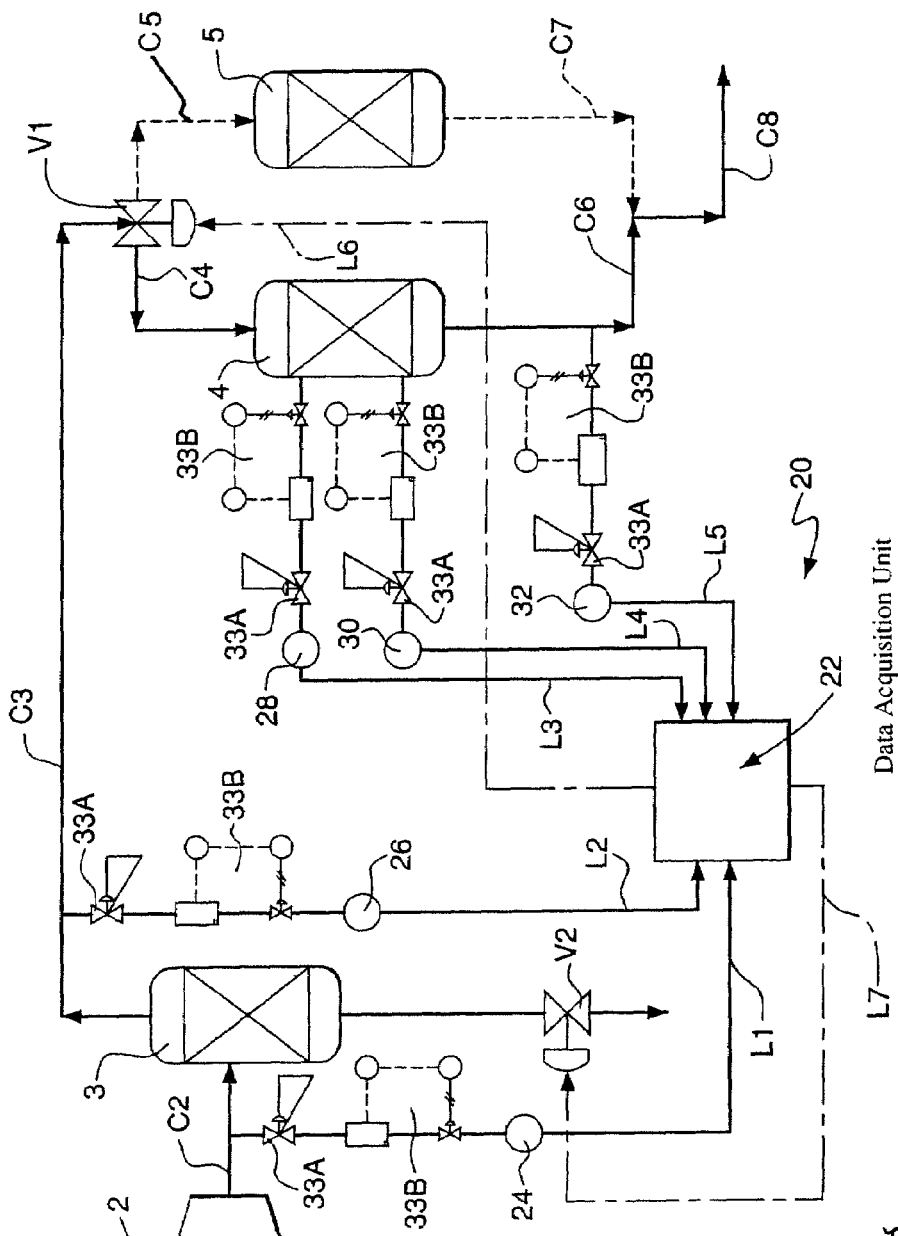
FIG. 1 is a schematic view of an exemplary embodiment of the detection system of the subject invention shown in an exemplary embodiment of a conventional gas system.

Referring now to the various figures of the drawing wherein like reference numbers refer to like parts, there is shown in FIG. 1 one exemplary embodiment of a fine liquid particle/droplet detection system 20 constructed in accordance with this invention. The system 20 is particularly arranged to be used in any gas system 1, e.g., a cryogenic system, making use of at least one high pressure gas compressor or other device which may introduce fine oil particles into the gas. However, such a cryogenic application is merely exemplary of a myriad of gas systems that can make expeditious use of the subject invention. Moreover, while the subject detection system of this invention will be described for detecting fine particles of oil that also is merely exemplary. Thus, the detection system 20 can be used for detecting any type of particles which may tend to leak or be accidentally introduced into a gas system 1.

Before describing the detection system 20, a brief description of the exemplary gas system 1 is in order. It must, at this juncture, be pointed out that the embodiment of the system 1 shown herein is merely exemplary of various embodiments of gas systems including high pressure compressors or other devices which may introduce fine oil or other particles into the gas which could make use of the subject invention. Thus, the subject invention can be used in any gas system having a compressor or any other device which is susceptible to introducing oil particles or other undesirable liquid particles into a gas, wherein that system includes one or more coalescers, separators, adsorbent beds and filters. In the exemplary embodiment of FIG. 1, the gas system 1 basically comprises a high pressure compressor 2 and a plurality of devices, e.g., a coalescer 3 and a pair of adsorbers 4 and 5, connected down stream of the compressor 2 for performing various standard functions well known in the art and not to be repeated here in the interest of brevity.

The compressor 2 has an input gas-carrying line or conduit C1 connected to it to carry the gas to be compressed to the compressor, and an output gas-carrying line or conduit C2 for carrying the compressed gas from the compressor to the downstream components (in this exemplary embodiment to the coalescer 3). As mentioned above, the operation of the compressor will likely result in the creation of fine oil particles in the compressed gas. It is such particles that the detection system 20 of this invention is arranged to detect so that corrective action can be taken. The output of the coalescer 3 is provided by a gas-carrying line or conduit C3 to the adsorbers 4 and 5. In particular, the gas-carrying line or conduit C3 is connected to the input of a diverter valve V1 having a pair of selectable outlets connected to respective gas-carrying lines or conduits C4 and C5 (conduit C5 being shown by broken lines for reasons to be discussed later). The output of the adsorber C4 is provided via an output gas-carrying line or conduit C6. In a similar manner, the output of the adsorber 5 is provided via an output gas-carrying line or conduit C7 (also shown by broken line for reasons to be discussed later). The lines or conduits C6 and C7 merge into a combined gas-carrying line or conduit C8 which may be connected to any other piece of equipment, e.g., a storage tank, etc., of the gas system 1.

The coalescer 33 includes a blow-down port to which a blow-down valve V2 is connected. The valve V2 is arranged to drain or otherwise enable the discharge of gas containing oil particles to means (not shown) in it when called upon to do so by the detection system 20 as will be described later. The diverter valve V1 is arranged to selectively switch the adsorber 5 into the downstream gas path from the coalescer in case the adsorber 4 has an undesirable amount of oil particles trapped within it. The switching from the adsorber 4 to the other adsorber 5 is determined by the operation of the system 20 as will be described later. In the embodiment shown in FIG. 1, it is assumed that the diverter valve V1 is in the position so the gas from the coalescer output conduit C3 is provided through the valve to the conduit C4 serving as the input of the adsorber 4. In this valve position, the flow of gas from the coalescer conduit C3 is prevented from flowing into the conduit C5 to the adsorber 5. Thus, the input conduit C5 to the adsorber 5 and the outlet conduit C7 from the adsorber 5 are shown by broken lines to represent that that part of the system is off-line at this time.

The exemplary system 1 shown and described above, for example, comprises a "closed-loop" system, i.e., the valves are arranged to be automatically controlled by the detection system 20, as will be described later. However, that too is merely exemplary. Thus, one or more of the valves forming the gas system 1 can be manually controlled by some personnel, with such control being determined by the state of the gas system 1 as detected by the detecting system 20.

The detection system 20 basically comprises a data acquisition unit 22 and plural particulate detection monitors 24, 26, 28, 30 and 32, each monitor making use of a high sensitivity nephalometric (photometric) sensor. The monitors 24, 26, 28, 30 and 32 are connected to the data acquisition unit via respective lines L1, L2, L3, L4 and L5. The data acquisition unit may be any conventional device, such as data logger, a computer or a portion of a distributed control system (DCS) of the facility operating the system 1. One particularly suitable particle commercially available monitor unit for making up the monitors 24, 26, 28, 30 and 32 is the above mentioned HPM-1000 particulate monitor of Thermo Andersen, Inc. As mentioned above, this monitor and its associated sensor is designed to measure the concentration of gas borne particulate matter (liquid or solid), at pressures up to 350 psig. The high sensitivity nephalometric (photometric) sensors' light scattering detection configuration of this invention is optimized for the measurement of fine particle contamination in compressed air and gas streams. Thus, the system 20 is designed to work within the following parameters: Sample Pressures: 0 psig-350 psig. Sample Flow Rates: 1 L/min-30 L/min. Sensor Electrical Requirements: 90-265 VAC, 50-60 Hz. Measurement Range: 0.01 mg/m3 to 400 mg/m3 or 0.03 ug/ft3 to 11,330 ug/ft3. It should be pointed out at this juncture that other oil or other liquid or solid particle monitors can be used in lieu of the HPM-1000 monitor.

Figure 2:
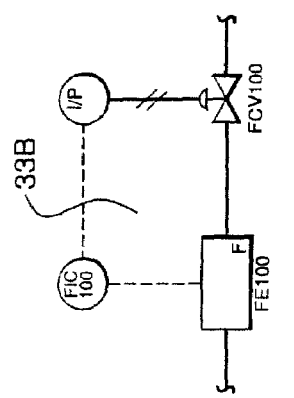
FIG. 2 is a schematic view of the pressure control valve and associated components shown in FIG. 1.

The HPM-1000 high pressure particulate monitor is specified by its manufacturer as being capable of measurement and calibration independent of flow rate. However, it has been discovered that for optimal effective and accurate usage, particularly in closed loop process control systems, like the exemplary one shown herein, the flow rate and pressure be controlled. Thus, in the exemplary embodiment disclosed herein the input to each HPM1-1000 monitor 24, 26, 28, 30 and 32 has an adjustable pressure and flow control means associated with it. Such adjustable pressure and flow control means can comprise any commercially available devices, such as a pressure control valve 33A and a flow control valve and associated components collectively designated by the reference number 33B and shown in more detail in FIG. 2. Such devices are available from Swagelock Company of Solon, Ohio, Parker Hannifin Corporation of Cleveland, Ohio and others. The valves 33A and 33B are connected in series between the monitor and the line, conduit or device carrying the gas to be monitored. The valves may be adjusted manually or under automated control from the data logger 22 or any other associated equipment. Each of the pressure and flow control means is arranged to control the flow within a range of approximately +/−2% for rates in the range of approximately 1 to 30 liters per minute, and to control the pressure within a range of +/−10 PSIG for pressures in the range of approximately 100 to 350 PSIG and approximately +/−5% of the value in the range of approximately 1 to 100 PSIG. As will be appreciated by those skilled in the art the settings for the pressure and flow are dependent upon the conditions of the system 1 in which the subject invention is to be used. Thus, the pressure and flow rate of the system 1 at each of the locations where the monitors of this invention are to be located should be determined and the appropriate setting of pressure and flow be made consistent therewith. Also, it is desirable to set the pressure as low as is consistent with the make-up of the system 1 to prevent the liquid particles/droplets from condensing out of the gas and onto the conduit, tubing or device(s) in which the gas passes. One exemplary setting for the pressure and flow could be a pressure of approximately 15 psi at a flow rate of approximately 25 liters/minute.

The monitor 24 is located immediately downstream of the compressor 2 and is hence referred to as the post compressor monitor. It is coupled to the gas-carrying conduit C2 and to the data acquisition unit 22 via line L1 so that the system 20 can determine the existence and level of any oil particles within the gas in the conduit C2. The monitor 26 is located immediately downstream of the coalescer 3 and is hence referred to as the post coalescer monitor. It is coupled to the gas-carrying conduit C3 and to the data acquisition unit 22 via line L2 so that the system 20 can determine the existence and level of any oil particles within the gas in the conduit C3. The monitor 28 is located at an upstream portion of the adsorber 4 and is coupled to the interior thereof and to the data acquisition unit 22 via line L3 so that the system 20 can determine the existence and level of any oil particles within the gas in that upstream portion of the adsorber 4. The monitor 30 is located at a downstream location of the adsorber 4 and is coupled to the interior thereof and to the data acquisition unit 22 via line L4 so that the system 20 can determine the existence and level of any oil particles within the gas in that downstream portion of the adsorber 4. The monitor 32 is located downstream of the outlet of the adsorber 4, i.e., it is coupled to the gas-carrying conduit C6 and to the data acquisition unit 22 via line L5 so that the system 20 can determine the existence and level of any oil particles within the gas in the conduit C6. Thus, the data acquisition unit 22, be it a data logger, a computer, a portion of a DCS or some other device, is arranged to receive signals, e.g., multiplexed signals, from the monitors, to analyze those signals and to provide alert and/or control signals as will be described later to enable the gas producing, transport and/or storage system 1 to be maintained in a condition wherein the level of oil or other liquid particle/droplets is below a desired threshold level.

The monitoring system 20 and the methods of this invention enable the detection of extremely low levels of oil or other liquid contaminant particles. If higher than normal levels of oil or other liquid contaminant particles are detected, the system is arranged to take corrective action (e.g., alert operators and/or switch an associated valve to send feed to another bed to prevent the oil or other liquid contaminant being passed into the final product). In addition the system allows a more optimum usage of existing adsorbent beds, coalescers and filters. To that end, the data acquisition unit 22 is arranged to provide information, e.g., alerts, regarding the level of oil particles detected by any of its connected sensors and to provide that information to operating personnel so that corrective action can be taken. While the corrective action can be accomplished manually, e.g., a person going to the sensed location and opening a valve associated with the device which has exhibited an undesirable amount of oil particles, automatic control is desirable in many cases. Thus, as mentioned above in one exemplary embodiment of the system 20 described heretofore is a close-loop system so that corrective action can be undertaken automatically. To that end the data acquisition unit 22 includes various output lines for automatically controlling the operation of the associated valves V1 and V2 in the system 1 and those valves are constructed and arranged to enable automatic control. In particular, one output line of the data acquisition unit 22 is designated as control line L6 and is connected to the diverter valve V1. The control line L6 is shown in phantom in the interest of drawing clarity. The valve V1 is arranged to selectively switch the gas-carrying conduit C3 into communication with either gas-carrying conduit C4 or C5 depending upon the control signal provided from the data acquisition unit 22 via control line L6. In the normal operational sequence shown in FIG. 1, the valve V1 is in the state wherein the adsorber 4 is on-line (i.e., switched into communication with the gas-carrying conduit C3), while the adsorber 5 is off-line (i.e., switched out of communication with the gas-carrying conduit C3), but available if needed to be switched in.

One exemplary mode of operation of the system 20 is as follows. The data acquisition unit 22 receives signals from the post compressor monitor 24 via line L1 and also receives signals from the post coalescer monitor 26 via line L2. Those two input signals are compared to determine the oil mist breakthrough post coalescer. If the level at that point is excessive, e.g., exceeds a predetermined threshold amount, then the system 20 produces an alert signal. That signal can be used by an operator to open the blow-down valve V2, but normally a control signal is sent from the monitor unit via line L7 to the blow-down valve V2 to directly (i.e., automatically) open it until the oil level in the post coalescer gas-carrying conduit C3 returns to a desired nominal value. The system is also arranged to monitor the oil level at the location of monitors 28, 30 and 32 associated with the on-line adsorber (bed) 4 and to provide respective signals via lines L3, L4 and L5 to the data acquisition unit 22 representative of the detected oil levels. The data acquisition unit 22 can then compare any of those signals to the signal provided by the post coalescer monitor 26 to determine the relative oil mist breakthrough through the adsorber 4 (if such is the case). If a high level of oil is found at the output of the adsorber 4, i.e., within gas-carrying conduit C6, the data acquisition unit 22 can automatically provide an output signal via line L6 to the diverter valve V1, whereupon the valve will switch states, to take the adsorber 4 off-line and place the adsorber 5 on-line, i.e., shut off the flow of gas from gas-carrying conduit C3 to the adsorber 4 and enable gas to flow from that conduit to the adsorber 5. Alternatively, the monitor unit 22 can provide an alert signal to an operator so that a person can be dispatched to switch the diverter valve V1 to the second bed, i.e., adsorber 5 and thus prevent oil breakthrough. Moreover, the amount of bed remaining free of oil can be determined by comparing the oil level at points associated with the monitors 26, 28 and 30 or at additional monitor connection points.

Further still, the system of this invention enables one to readily determine if there is a very high concentration of liquid, e.g., oil, particles/droplets in the gas, since such an occurrence will result in the condensation of the liquid on the side of the tubing carrying the gas, whereupon there will be a precipitous drop in the particles/droplets detected by the monitor(s). Accordingly, the detection of a precipitous drop in particles/droplets detected can be used by the data logger 22 to provide appropriate warning (alert) signals to operating personnel or control signals to take automated corrective action.

For some applications wherein any of the monitors will be subjected to substantial vibration, e.g., a monitor mounted on or near a particular vibration prone compressor, it may be desirable to make use of conventional vibration isolator to ensure proper monitor operation. One particularly suitable isolator for that purpose is the 6M MICRO/LEVEL® Elastomer Isolator available from VIBRO/DYNAMICS Corporation of Broadview, Ill.

As should be appreciated by those skilled in the art, with the system 20 as shown and described control for the blow down valve V2 can be readily achieved by monitoring the gas via monitors 24 and 26, whereupon the valve V2 can be opened if high levels of oil carryover are detected. Control for the diverter valve V1 can be readily achieved by monitoring the gas via monitors 28, 30 and 32, whereupon the valve V1 can be switched to bring the auxiliary bed (adsorber) 5 on line if high levels of oil are detected by monitor 32. Preparation to bring the adsorber 5 on line via valve V1 can be effected by means of operation of the monitor 30. Further still, use of the monitors 28 and 30 enable the system to assess available bed left and time to breakthrough. Moreover, the data acquisition unit which is coupled to the monitors can be used to alert operators of the system 20 so that maintenance can be accomplished, as needed. In short, the subject invention enables the accurate estimation of adsorbent bed life and can be used to optimize/maximize the amount of time a bed could be used without any oil breakthrough. In essence the use of multiple-point sampling with alarm/control of this invention allows for early detection of oil mist breakthrough, equipment mal-performance, and maximizing of the current equipment utilization, while providing a gas product that exhibits the proper specifications.

While the invention has been described in detail and with reference to specific examples thereof, it will be apparent to one skilled in the art that various changes and modifications can be made therein without departing from the spirit and scope thereof.

The invention claimed is:

1. A detection system for detecting the presence of fine liquid particles in a gas system, the gas system comprising a compressor or other device which may introduce fine oil particles into a gas and at least a first gas handling device and a second gas handling device, a first gas-carrying conduit connected between the compressor or other device and the first device and a second gas-carrying conduit connected between the first device and the second device, the first and second devices being connected in series downstream of the compressor or other device by the gas-carrying conduits, the first device having a first valve associated with the first device, the second device having a second valve associated with the second device, the compressor or other device being susceptible to introduce fine liquid particles into the first gas-carrying conduit, said detection system comprising a data acquisition unit and at least a first monitor and a second monitor, each of said monitors being arranged for detecting the presence of fine liquid particles in the gas by means of light scattering and for providing an output signal to said data acquisition unit in response to the detection of such fine liquid particles, said first monitor being in communication with the interior of the first gas-carrying conduit, said second monitor being in communication with the interior of the second gas-carrying conduit, said data acquisition unit being arranged to provide at least one output signal concerning the detection of fine liquid particles in the gas system.

2. The detection system of claim 1 wherein said at least one output signal of said data acquisition unit comprises a humanly perceptible signal.

3. The detection system of claim 1 wherein said at least one output signal of said data acquisition unit is coupled to the first and second valves for effecting the selective operation of said valves.

4. The detection system of claim 1 wherein said data acquisition unit compares said output signal from said second monitor to said output signal from said first monitor and provides a first output signal when the level of fine liquid particles detected by said second monitor exceeds by a predetermined amount the level of fine liquid particles detected by said first monitor.

5. The detection system of claim 1 wherein said first valve is a blow-down valve and wherein the gas system additionally comprises a third device connected in parallel to the second device by the second valve, the second valve being a diverter valve and being coupled to the second gas-carrying conduit, the second valve being settable to enable the second device to be normally in fluid communication with said first device via the second gas-carrying conduit, said detection system additionally comprising a third monitor arranged for detecting the presence of fine liquid particles in a gas by means of light scattering and for providing an output signal to said data acquisition unit in response to the detection of such fine liquid particles, said third monitor being coupled to said data acquisition unit and to the second device for detecting the presence of fine liquid particles in the second device.

6. The detection system of claim 5 wherein said data acquisition unit compares said output signal from said second monitor to said output signal from said first monitor and provides a first output signal when the level of fine liquid particles detected by said second monitor exceeds by a predetermined amount the level of fine liquid particles detected by said first monitor, and wherein said data acquisition unit also compares said output signal from said third monitor to said output signal from said second monitor and provides a second output signal when the level of fine liquid particles detected by said third monitor exceeds by a predetermined amount the level of fine liquid particles detected by said second monitor.

7. The detection system of claim 5 additionally comprises a fourth monitor arranged for detecting the presence of fine liquid particles in a gas by means of light scattering and for providing an output signal to said data acquisition unit in response to the detection of such fine liquid particles, said fourth monitor being coupled to the data acquisition unit and to the second device downstream of said third monitor for detecting the presence of fine liquid particles in the second device downstream of the location of said third monitor.

8. The detection system of claim 7 wherein said data acquisition unit compares said output signal from said second monitor to said output signal from said first monitor and provides a first output signal when the level of fine liquid particles detected by said second monitor exceeds by a predetermined amount the level of fine liquid particles detected by said first monitor, wherein said data acquisition unit compares said output signal from said third monitor to said output signal from said second monitor and provides a second output signal when the level of fine liquid particles detected by said third monitor exceeds by a predetermined amount the level of fine liquid particles detected by said second monitor and wherein said data acquisition unit compares said output signal from said fourth monitor to said output signal from said second monitor and provides a third output signal when the level of fine liquid particles detected by said fourth monitor exceeds by a predetermined amount the level of fine liquid particles detected by said second monitor.

9. The detection system of claim 7 wherein the second device includes an outlet and wherein said detection system additionally comprises a fifth monitor arranged for detecting the presence of fine liquid particles in a gas by means of light scattering and for providing an output signal to said data acquisition unit in response to the detection of such fine liquid particles, said fifth monitor being coupled to said data acquisition unit and to the outlet of the second device downstream of said fourth monitor for detecting the presence of fine liquid particles at the outlet of the second device.

10. The detection system of claim 9 wherein said data acquisition unit compares said output signal from said second monitor to said output signal from said first monitor and provides a first output signal when the level of fine liquid particles detected by said second monitor exceeds by a predetermined amount the level of fine liquid particles detected by said first monitor, wherein said data acquisition unit compares said output signal from said third monitor to said output signal from said second monitor and provides a second output signal when the level of fine liquid particles detected by said third monitor exceeds by a predetermined amount the level of fine liquid particles detected by said second monitor, wherein said data acquisition unit compares said output signal from said fourth monitor to said output signal from said second monitor and provides a third output signal when the level of fine liquid particles detected by said fourth monitor exceeds by a predetermined amount the level of fine liquid particles detected by said second monitor and wherein said data acquisition unit compares said output signal from said fifth monitor to said output signal from said second monitor and provides a fourth output signal when the level of fine liquid particles detected by said fifth monitor exceeds by a predetermined amount the level of fine liquid particles detected by said second monitor.

11. The detection system of claim 7 wherein said first monitor is in communication with the first gas-carrying conduit via adjustable first pressure and flow control means, said second monitor is in communication with the second gas-carrying conduit via adjustable second pressure and flow control means, said third monitor is in communication with the second device via adjustable third pressure and flow control means, and said fourth monitor is in communication with the second device via adjustable fourth pressure and flow control means, said adjustable first, second, third and fourth pressure and flow control means being arranged to be adjusted in response to a signal from said data acquisition unit.

12. The detection system of claim 11 wherein said adjustable first, second, third and fourth pressure and flow control means are coupled to said data acquisition unit and are arranged to be adjusted in automatic response to a signal from said data acquisition unit.

13. The detection system of claim 5 wherein said first monitor is in communication with the first gas-carrying conduit via adjustable first pressure and flow control means, said second monitor is in communication with the second gas-carrying conduit via adjustable second pressure and flow control means, and said third monitor is in communication with the second device via adjustable third pressure and flow control means, said adjustable first, second and third pressure and flow control means being arranged to be adjusted in response to a signal from said data acquisition unit.

14. The detection system of claim 13 wherein said adjustable first, second and third pressure and flow control means are coupled to said data acquisition unit and are arranged to be adjusted in automatic response to a signal from said data acquisition unit.

15. The detection system of claim 1 wherein said first monitor is in communication with the first gas-carrying conduit via adjustable first pressure and flow control means and said second monitor is in communication with the second gas-carrying conduit via adjustable second pressure and flow control means, said adjustable first and second pressure and flow control means being arranged to be adjusted in response to a signal from said data acquisition unit.

16. The detection system of claim 15 wherein said adjustable first and second pressure and flow control means are coupled to said data acquisition unit and are arranged to be adjusted in automatic response to a signal from said data acquisition unit.

17. The detection system of claim 15 wherein the first pressure and flow control means is arranged to control the flow within a range of approximately +/−2% for rates in the range of approximately one to thirty liters per minute, and to control the pressure within a range of +/−10 PSIG for pressures in the range of approximately 100 to 350 PSIG and approximately +/−5% of the value in the range of approximately 1 to 100 PSIG.

18. A detection system for particles in a gas system, the gas system comprising a compressor or other device which may introduce particles into a gas and at least a first gas handling device and a second gas handling device, a first gas-carrying conduit connected between the compressor or other device and the first device and a second gas-carrying conduit connected between the first device and the second device, the first and second devices being connected in series downstream of the compressor or other device by the gas-carrying conduits, the first device having a first valve associated with the first device, the second device having a second valve associated with the second device, and said detection system comprising a data acquisition unit and at least a first monitor and a second monitor, each of said monitors being arranged for detecting the presence of particles in the gas and for providing an output signal to said data acquisition unit in response to the detection of such particles, said first monitor being in communication with the interior of the first gas-carrying conduit, said second monitor being in communication with the interior of the second gas-carrying conduit, said data acquisition unit being arranged to provide at least one output signal concerning the detection of particles in the gas system.

19. A method of detecting the presence of fine liquid particles in a gas system, the gas system comprising a compressor and at least a first gas handling device and a second gas handling device, a first gas-carrying conduit connected between the compressor and the first device and a second gas-carrying conduit connected between said first device and said second device, said first and second devices being connected in series downstream of said compressor by said gas-carrying conduits, said first device having a first valve associated with said first device, said second device having a second valve associated with said second device, said method comprising:

detecting the presence of fine liquid particles in a gas between said compressor and said first device by means of light scattering and providing a first output signal in response to the detection of such fine liquid particles, detecting the presence of fine liquid particles in a gas between said first device and said second device by means of light scattering and providing a second output signal in response to the detection of such fine liquid particles, and;

utilizing said first and second output signals to provide at least one alert signal that can be utilized to enable the selective operation of said valves.

20. The method of claim 19 wherein the first valve is a blow-down valve and wherein said gas system additionally comprises a third device connected in parallel to said second device by said second valve, said second valve being a diverter valve and being coupled to said second gas-carrying conduit, said second valve being settable to enable said second device to be normally in fluid communication with said first device via said second gas-carrying conduit, said method additionally comprising:

detecting the presence of fine liquid particles in said gas at an upstream location within said second device and providing a third output signal in response to the detection of such fine liquid particles.

21. The method of claim 20 additionally comprising:

comparing said first output signal to said second output signal and providing a first alert signal when the level of fine liquid particles in said gas between said first device and said second device exceeds by a predetermined amount the level of fine liquid particles in said gas between said compressor and said first device; and comparing said third output signal to said second output signal and providing a second alert signal when the level of fine liquid particles in said gas in said second device exceeds by a predetermined amount the level of fine liquid particles in said gas between said first device and said second device.

22. The method of claim 21 wherein the first valve is a blow-down valve and wherein said second device comprises an outlet and wherein said gas system additionally comprises a third device connected in parallel to said second device by said second valve, said second valve being a diverter valve and being coupled to said second gas-carrying conduit, said second valve being settable to enable said second device to be normally in fluid communication with said first device via said second gas-carrying conduit, said method additionally comprising:

detecting the presence of fine liquid particles in said gas at said outlet of said second device and providing a fourth output signal in response to the detection of such fine liquid particles;

comparing said first output signal to said second output signal and providing a first alert signal when the level of fine liquid particles in said gas between said first device and said second device exceeds by a predetermined amount the level of fine liquid particles in said gas between said compressor and said first device; and comparing said fourth output signal to said second output signal and providing a fifth alert signal when the level of fine liquid particles in said gas at said outlet of said second device exceeds by a predetermined amount the level of fine liquid particles in said gas between said first device and said second device.

23. The method of claim 19 additionally comprising controlling the pressure and the flow of the gas between said compressor and said first device and controlling the pressure and the flow of the gas between said first device and said second device to facilitate detecting the presence of fine liquid particles between said compressor and said first device and between said first device and said second device.

24. The method of claim 23 wherein control of the flow of the gas is within a range of approximately +/−2% for rates in the range of approximately one to thirty liters per minute and wherein the control of pressure of the gas is within a range of +/−10 PSIG for pressures in the range of approximately 100 to 350 PSIG and approximately +/−5% of the value in the range of approximately 1 to 100 PSIG.

\* \* \* \* \*